United States Patent [19]

de Castiglione et al.

[11] Patent Number: 4,567,162

[45] Date of Patent: Jan. 28, 1986

[54] BIOLOGICALLY ACTIVE HEPTAPEPTIDES

[75] Inventors: Robertó de Castiglione, Milan; Giuseppe Perseo, Desio; Mauro Gigli; Barbara Hecht, both of Milan, all of Italy

[73] Assignee: Farmitalia Carlo Erba, Milan, Italy

[21] Appl. No.: 624,820

[22] Filed: Jun. 26, 1984

[30] Foreign Application Priority Data

Jul. 13, 1983 [GB] United Kingdom ............... 8319174

[51] Int. Cl.$^4$ ................ A61K 37/00; C07C 103/52
[52] U.S. Cl. .......................... 514/16; 260/112.5 R
[58] Field of Search ................ 260/112.5 R; 514/16

[56] References Cited

U.S. PATENT DOCUMENTS 4,474,765 10/1984 de Castiglione et al. .... 260/112.5 R

Primary Examiner—Delbert R. Phillips

Attorney, Agent, or Firm—Oblon, Fisher, Spivak, McClelland & Maier

[57] ABSTRACT

There are provided peptides of the formula

X-Val-Pro-Leu-Gly-Trp-A-Y wherein X represents a hydrogen atom or a terminal nitrogen protecting group, A represents a neutral L-α-amino acid residue and Y represents OH, NH$_2$ or a group of the formula OR, NHR, NR$_2$ or NHNHR' wherein R represents a C$_1$-C$_{11}$ alkyl group optionally substituted, a C$_7$-C$_{14}$ aralkyl or a phenyl group and R' represents H, any of the groups which R may represent or a protecting group. Pharmaceutically or veterinarily acceptable salt of these peptides are also provided, as are pharmaceutical or veterinary compositions containing peptides or their salts. The peptides which can be prepared by classical solution synthesis, display useful activity on the central nervous system and are active as growth promotors.

23 Claims, No Drawings

BIOLOGICALLY ACTIVE HEPTAPEPTIDES

BACKGROUND OF THE INVENTION

The invention relates to biologically active peptides and their pharmaceutically or veterinarily acceptable salts, and to processes for their preparation and to pharmaceutical or veterinary compositions containing them.

SUMMARY OF THE INVENTION

In this Specification, the symbols and abbreviations used are those commonly used in peptide chemistry. (See Biochemistry (1975) 14, 449.)

The invention relates to compounds which are useful in promoting growth activity in animals and improving their feed efficiency. These compounds are useful with animals used for food such as fowl, ruminants, swine, and rabbits. These compounds which also exhibit endocrinological activity and activity on the central nervous system may be administered using methods known in the art such as mixing in feed rations, subcutaneous implants, etc.

The invention provides peptides having the general formula:

X-Val-Pro-Pro-Leu-Gly-Trp-A-Y wherein
X represents a hydrogen atom or a terminal nitrogen protecting group of acyl, aliphatic urethane, aromatic urethane, alkyl or aralkyl type;
A represents a neutral L-α-amino acid residue; and
Y represents a hydroxy group, an amino group or a group of the formula OR, NHR, NR$_2$ or NH—NH—R' wherein R represents a straight chain, branched chain or cyclic (including fused or bridged rings) alkyl group having up to 11 carbon atoms which may be unsubstituted or independently substituted by a hydroxy or amino group or a halogen atom, an aralkyl group having from 7 to 14 carbon atoms or a phenyl group; and R' represents a hydrogen atom, any of the groups which R may represent, a straight chain, branched chain or cyclic aliphatic acyl group having from 1 to 11 carbon atoms which may be unsubstituted or independently substituted by a hydroxy or an amino group or a halogen atom, an aromatic acyl group which may be unsubstituted or independently substituted by a hydroxy or amino group or a halogen atom, a straight chain, branched chain or cyclic aliphatic urethane type group having from 3 to 11 carbon atoms, or an aromatic urethane type group.

The invention will now be illustrated by the following examples which are not intended to be limiting thereof.

DESCRIPTION OF THE PREFERRED EMBODIMENTS

Preferred terminal nitrogen atom protecting groups which X may represent include (of acyl type) formyl, acetyl, trifluoroacetyl, propionyl and benzoyl groups; (of aromatic urethane type) benzyloxycarbonyl (Z), 4-nitrobenzyloxycarbonyl, 4-methoxybenzyloxycarbonyl, 2,4-dichlorobenzyloxycarbonyl, 2-bromobenzyloxycarbonyl, 9-fluorenylmethoxycarbonyl (Fmoc) and 3,5-dimethoxy-α,α'-dimethylbenzyloxycarbonyl (Ddz) groups; (of aliphatic urethane type) t-butoxycarbonyl, 1-methylcyclobutoxycarbonyl, adamantyloxycarbonyl, isobornyloxycarbonyl and methylsulphonylethoxycarbonyl (Msc) groups; and (of alkyl and aralkyl type) trityl, benzyl, methyl and isopropyl groups. Acyl type groups which X may represent are preferably —CO—(C$_2$ TO C$_4$ alkyl). Alkyl groups which X may represent are preferably C$_1$ to C$_4$ alkyl. Aralkyl groups which X may represent are preferably a methyl group which can be substituted by 1 to 3 phenyl rings.

Preferred L-α-amino acid residues which A may represent include Met, Nle, Ile, Leu and Phe.

Preferred groups which R may represent include methyl, ethyl, n-propyl, isopropyl, n-butyl, s-butyl, isobutyl, t-butyl, 2,2,2-trifluoroethyl, cyclohexyl, adamantyl, phenyl, benzyl, phenethyl, and fluorenylmethyl groups. Examples of acyl groups which R' may represent are formyl, acetyl, trifluoroacetyl, propionyl, butyryl, adamantylcarbonyl, benzoyl, phenylacetyl and cinnamyl. The aliphatic and aromatic urethane type groups which R' may represent are preferably those groups mentioned as preferred terminal nitrogen protecting groups X of aliphatic and aromatic urethane type.

In the substitents of alkyl or acyl group which Y may represent, the term "halogen" should be construed to preferably encompass chlorine, bromine and fluorine atoms, and also an iodine atom.

Salts of peptides according to the invention with pharmaceutically acceptable acids or bases are within the scope of the invention. Such acid addition salts can be derived from a variety of inorganic and organic acids such as sulphuric, phosphoric, hydrochloric, hydrobromic, hydroiodic, nitric, sulphamic, citric, lactic, pyruvic, oxalic, maleic, succinic, tartaric, cinnamic, acetic, trifluoroacetic, benzoic, salicylic, gluconic and ascorbic acids. Such base addition salts can be derived from a variety of inorganic and organic bases such as sodium hydroxide, potassium hydroxide, diethylamine, triethylamine and dicyclohexylamine.

The synthesis of the peptides of the invention may be accomplished by classical solution methods. The synthesis consists essentially of appropriate successive condensations of protected amino acids or peptides. The condensations are carried out so that the resulting peptides have the desired sequence of seven amino acid residues. The amino acids and peptides, which are condensed according to methods known in polypeptide chemistry, have their amino and carboxyl groups, which are not involved in the formation of peptide linkage, blocked by a suitable protecting group. The protecting groups are capable of being removed by acidolysis, saponification and hydrogenolysis. The following groups may be used for the protection of amino groups: benzyloxycarbonyl, t-butoxycarbonyl, trityl, formyl, trifluoroacetyl, o-nitrophenylsulphenyl, 4-methoxybenzyloxycarbonyl, 9-fluorenylmethoxycarbonyl, 3,5-dimethoxy-α,α'-dimethylbenzyloxycarbonyl and methylsulphonylethoxycarbonyl. The following groups may be used for the protection of carboxy groups: methyl, ethyl, t-butyl, benzyl, p-nitrobenzyl and fluorenylmethyl.

The condensation between an amino group of one molecule and a carboxyl group of another molecule to form the peptidic linkage may be carried out through an activated acyl-derivative such as a mixed anhydride, an azide or an activated ester, or by direct condensation between a free amino group and a free carboxyl group, in the presence of a condensing agent such as dicyclohexylcarbodiimide, alone or together with a racemization preventing agent, such as N-hydroxysuccinimide or 1-hydroxybenzotriazole. The condensation may be carried our in a solvent such as dimethylformamide, pyridine, acetonitrile, tetrahydrofuran or N-methyl-2-pyrrolidone. The reaction temperature may be from −30° C. to ambient temperature. The reaction time is generally from 1 to 120 hours. The scheme of synthesis, the protecting groups and the condensing agents are selected so as to avoid the risk of racemization.

De-protecting reactions are carried out according to methods known per se in polypeptide chemistry. Peptides wherein Y represents OR are prepared, for example, starting from the C-terminal amino acid esterified by the appropriate alcohol. Peptides wherein Y represents OH can be prepared, for example, by hydrolysis of peptides wherein Y represents OR. Peptides wherein Y represents $NH_2$, NHR or $NR_2$ can be prepared by ammonolysis of the corresponding esters or starting from a C-terminal amino acid amidated by an appropriate amine. Hydrazido or substituted hydrazido derivatives according to the invention are prepared by condensation of the N-protected peptide or amino acid with a suitably substituted hydrazine, such as benzylcarbazate, t-butylcarbazate, adamantylcarbazate, phenylhydrazine or adamantylhydrazine, or reacting the N-protected peptide or amino acid hydrazide with a suitable alkylating agent, such as an alkyl chloride, or with a suitable acylating agent such as benzylchloroformate, t-butylchloroformate, di-t-butyldicarbonate or adamantylfluoroformate. The final condensation in the preparation of a peptide according to the invention is preferably between a compound of formula II: X-Val-Pro-Pro-OH, in the presence of a condensing agent such as dicyclohexylcarbodiimide, alone or together with a racemization preventing agent, or a mixed anhydride, activated ester or azide derivative of the compound of formula II as defined above, and a compound of formula III: H-Leu-Gly-Trp-A-Y, wherein A, X and Y are as herein defined save that X does not represent a hydrogen atom and Y does not represent a hydrazine group. The compounds according to the invention show an interesting growth promoting activity in animals determined both by the in vivo-in vitro test system on protein synthesis of liver tissue (as described by K. Kämmerer and A. Dey-Hazra (1980) Vet. Med. Nachr. Nr. 2, 99–112), and by the dose-dependent increase in weight gain and feed efficiency after subcutaneous or oral administration.

In vivo-in vitro test-Protein synthesis

The growth tests were carried out for periods of 4 weeks, using groups of 6 male rats (Wistar, Hagemann, Extertal) divided in subgroups of three animals managed in Markolon cages, good shaving as litter.

Water and feed (Altromin 1321 Standard diet containing 19% crude protein): ad libitum.

The peptides of the present invention were administered in solution s.c. daily at doses of 10, 50 and 100 ng/kg, using as diluent normal saline (starting from a stock solution with 100 ng/ml).

Preparation of Tissue Samples

Homogenise 3 g liver in 9 ml TKM buffer-saccharose solution, cooled on ice, in a Potter homogeniser at 600 r.p.m. for 2 min.; centrifuge at 4° C. in an ultracentrifuge with 10,000 g for 20 min., decant the supernatant-=microsomal cell juice.

Working procedure

After calculation of protein content in the microsomal cell juice by means of the biuret method, the protein concentration was adjusted with TKM buffer to 1 mg/ml. To that, a further dilution with bidistilled water to 0.25 mg protein per ml of the microsomal cell juice followed.

Subsequently portions of 0.15 l ml reaction medium and 0.05 ml (50 mcg) of pyruvate kinase solution, as well as 0.1 ml of $^{14}C$ amino acid mixture (=1 μCi) were added. The volume of the incubation mixture was then 1 ml each.

After a 35 minute incubation at 37° C. in a water bath, protein precipitation was performed by adding 2 ml of trichloracetic acid (10%). The sediment was washed by several additions of trichloroacetic acid and subsequent centrifugation (3600 g/5 min) until the supernatant was free from radioactivity.

The residue was dissolved in 1.0 ml Lumasolve and left overnight at 37° C., until it was clear.

Measuring the preparation was done in a PRIAS liquid scintillation counter PL (1.0 ml+5 ml scintillation liquid).

A detailed method is described in the above cited Kämmerer article.

TABLE 1

Results of the measurements of the protein synthesis rates of liver tissue of male rats after treatment for a period of 4 weeks (daily s.c. injection).

| Treatment with | Doses (ng/kg) | CPM | Δ % control rat group | |
|---|---|---|---|---|
| | | | untreated | treated |
| Compound of Ex. 1 (TK7) | 10 | 14072 | +17.7 | +36.1 |
| | 50 | 15093 | +26.2 | +46.0 |
| | 100 | 16180 | +35.3 | +56.5 |
| Compound of Ex. 2 (TK7D) | 10 | 13377 | +11.9 | +29.4 |
| | 50 | 14280 | +19.4 | +38.2 |
| | 100 | 16866 | +41.0 | +63.2 |
| Untreated control group | — | 11958 | — | — |
| Treated control group | — | 10336 | −13.6 | — |

CPM = counts per minute.

Control group

The rats treated with s.c. administration of physiological sodium chloride solution showed, in comparison with the untreated control group, a protein synthesis activity reduced by 13.6%.

That difference may be statically proved.

The measured protein synthesis rates of the compounds prepared in Examples 1 and 2 are significantly different from the two control groups.

Further, the increase of protein synthesis rates is directly related to dosages.

The compounds according to the invention show also interesting endocrinological activities such as prolactin and luteinizing hormone release. In addition they are endowed with activity on the central nervous system, particularly as sedative-hypnotics. In fact they are able to induce reduction of spontaneous activity and behavioural sleep in rats.

It is another embodiment of this invention to provide a method for promoting the growth of animals and improving their feed efficiency by administering to them a compound of this invention.

This method will be particularly suitable for animals raised for food such as fowl, ruminants, swine and rabbits.

Although all members of the fowl family—i.e. chickens, turkeys, geese, ducks, guinea fowl, pheasant and quail—will show increased rate of growth and improved feed efficiency, the method is particularly valuable for broiler chickens and turkeys.

Of the ruminants, e.g. cattle, sheep and goats, the method is particularly of value for cattle, e.g. steers.

A method of administration of a compound of this invention is to incorporate it in the feed rations intended for the animal at a concentration of from about 2 to 40 mcg/ton of feed, preferably from about 4 to 20 mcg/ton. The animals are permitted to feed at liberty throughout the growth period.

There are many specialized feed rations for different species of animals.

The compounds of this invention can be used with any of the known rations.

The term "feed rations" is intended to mean the food provided for the animals, and it is not intended that the invention be limited thereby. Preferably the compound is thoroughly mixed with the feed ration so that it is uniformly dispersed throughout. Any of the known feed rations can be used in the practice of this invention and it is not intended that the invention be limited by the formulation of the ration.

Feed rations are formulated to provide the animals for which they are intended with the essential nutrients, minerals, vitamins, bulk, etc.

Formulations of these rations are well within the skill of nutritionists.

Another method of administering the compounds of the present invention is by means of subcutaneously implant, e.g. in a pellet form of the peptides of the present invention to be subcutaneously injected to the animals with a release of substance per day in a range from 1 to 100 ng/kg, preferably from about 10 to 50 ng/kg.

Thus, it is not intended that the invention be limited to any particular mode of administration.

Accordingly, the invention further provides a pharmaceutical or veterinary composition comprising a compound of the invention or a pharmaceutically or veterinarily acceptable salt thereof in admixture with a pharmaceutically or veterinarily acceptable diluent or carrier; in addition, these preparations can have directed or delayed liberation of the active ingredient.

Veterinarily acceptable carrier refers to an edible material to which the peptides of the invention are added to facilitate uniform incorporation of such peptides into feeds.

The active peptide is adsorbed, impregnated or coated into or onto the edible material in such way as to disperse and physically carry the active peptide.

Preferred peptides according to the invention are reported below:

H-Val-Pro-Pro-Leu-Gly-Trp-Met-OH
H-Val-Pro-Pro-Leu-Gly-Trp-Met-OMe
H-Val-Pro-Pro-Leu-Gly-Trp-Met-NH$_2$
H-Val-Pro-Pro-Leu-Gly-Trp-Nle-OH
H-Val-Pro-Pro-Leu-Gly-Trp-Nle-OMe
H-Val-Pro-Pro-Leu-Gly-Trp-Nle-NH$_2$
H-Val-Pro-Pro-Leu-Gly-Trp-Leu-OH
H-Val-Pro-Pro-Leu-Gly-Trp-Leu-OMe
H-Val-Pro-Pro-Leu-Gly-Trp-Leu-NH$_2$
H-Val-Pro-Pro-Leu-Gly-Trp-Ile-OH
H-Val-Pro-Pro-Leu-Gly-Trp-Ile-OMe
H-Val-Pro-Pro-Leu-Gly-Trp-Ile-NH$_2$
H-Val-Pro-Pro-Leu-Gly-Trp-Phe-OH
H-Val-Pro-Pro-Leu-Gly-Trp-Phe-OMe
H-Val-Pro-Pro-Leu-Gly-Trp-Phe-NH$_2$

The following Examples are now given to illustrate the invention.

The Rf values were determined on pre-coated plates of silica gel 60 F$_{254}$ (Merck) layer thickness 0.25 mm, length 20 cm, using the following development systems:

System A: benzene/benzine (60–80)/ethyl acetate=70/10/40 by volume

System B: benzene/ethyl acetate/acetic acid/water=100/100/20/10 by volume (upper phase).

System C: benzene/ethyl acetate/acetic acid/water=100/100/40/15 by volume (upper phase).

System D: n-butanol/acetic acid/water=4/1/1 by volume.

"E. Merck" is a Trade Mark.

TLC analyses were carried out at a temperature ranging from 18° to 25° C.: the R$_f$ values can therefore change by ±5%. Melting points were determined in open capillaries with a Tottoli apparatus and are uncorrected. Most of the derivatives soften and decompose before melting. Solvents for crystallization, precipitation or grinding are reported in brackets.

High voltage paper electrophoresis is carried out with a Pherograph-Original-Frankfurt Type 64 apparatus on Schleicher and Schüll paper n. 2317 at pH 1.2 (formic acid:acetic acid:water=123:100:777 by volume) at 1600 V (40 V/cm), and at pH 5.8 (pyridine:acetic acid:water=450:50:4500 by volume) at 1400 V (32.5 V/cm). The products were characterized by their mobilities relative to Glu at pH 1.2 (E$_{1.2}$), and at pH 5.8 (E$_{5.8}$).

The symbols and abbreviations used in the following Examples are:

AcOEt, ethyl acetate; BOC, t-butoxycarbonyl; Bzl, benzyl; d, decomposition; DMF, dimethylformamide; Et$_2$O, diethyl ether; HCl/THF, hydrogen chloride in tetrahydrofuran; iPr$_2$O, diisopropyl ether; iPrOH, isopropanol; Me, methyl; MeOH, methanol; NMM, N-methylmorpholine; PE, petroleum ether; THF, tetrahydrofuran; TLC, thin layer chromatography.

EXAMPLE 1

Preparation of
H-Val-Pro-Pro-Leu-Gly-Trp-Met-OH.HCl, TK7
(XIII)

Step 1. BOC-Trp-Met-OMe (I)

To a solution of 30.43 g (100 mmol) of BOC-Trp-OH in 200 ml of anhydrous THF, 11.2 ml (100 mmol) of NMM and 9.9 ml of ethylchloroformate were successively added at a temperature of −12° C. After stirring at this temperature for 2 minutes, a cold solution of 19.96 g (100 mmol) of HCl.H-Met-OMe [C. A. Dekker et al, J. Biol.Chem. 180, 155 (1949)] and 11.2 ml of NMM (100 mmol) in 150 ml of DMF were added. The reaction mixture was stirred for 45 minutes at −12° C. and for 90 minutes at 0°–15° C., then filtered from salts and evaporated in vacuo. The residue was dissolved in ethyl acetate and washed several times successively with sodium chloride saturated solutions of 1M citric acid, 1M sodium bicarbonate and water. The organic layer was dried over anhydrous sodium sulphate and the solvent removed in vacuo.

39.12 g (87% yield) of compound I were obtained from iPrOH/iPr$_2$O/PE: m.p. 95°–97° C.; $[\alpha]_D^{20} = -25.1°$ (c=1, Me,OH); Rf$_A$ 0.73; Rf$_B$ 0.76.

Step 2. HCl.H-Trp-Met-Ome (II)

39.00 g (86.75 mmol) of BOC-Trp-Met-OMe (I) were dissolved in 390 ml of formic acid at room temperature.

After complete BOC-removal (TCL monitoring) the solvent was evaporated in vacuo at 30° C. The residue was dissolved in methanol cooled to 0° C. and 34.7 ml (104.1 mmol) of a 3M solution of HCl/THF were added. Solvents were removed in vacuo and 33.48 g (quantitative yield) of compound II were obtained as an oil, Rf$_D$ 0.71, E$_{1.2}$ 0.82.

Step 3. BOC-Gly-Trp-Met-OMe (III)

Starting from 15.20 g (86.75 mmol) of BOC-Gly-OH and 33.48 g (86.75 mmol) of HCl.H-Trp-Met-OMe (II), and operating as in Step 1 but using chloroform instead of ethyl acetate during the isolation of the product, 26.37 g (60% yield) of compound III were obtained from AcOEt/ET$_2$O/iPR$_2$O: m.p. 140°–145° C.; $[\alpha]_D^{20} = -30°$ (c=1, MeOH); Rf$_A$ 0.27; Rf$_B$ 0.56; Rf$_C$ 0.77.

Step 4. HCl.H-Gly-Trp-Met-OMe (IV)

Starting from 26.20 g (51.71 mmol) of BOC-Gly-Trp-Met-OMe (III) and operating as described in step 2, 21.76 g (95% yield) of compound IV were obtained from iPrOH/iPr$_2$O: m.p. 195° C. (d); $[\alpha]_D^{20} = -12.9°$ (c=1, MeOH); Rf$_D$ 0.49, E$_{1.2}$ 0.84.

Step 5. BOC-Leu-Gly-Trp-Met-OMe (V)

To a solution of 12.16 g (48.76 mmol) of BOC-Leu-OH in 120 ml of anhydrous THF, 5.5 ml (48.76 mmol) of NMM and 4.8 ml (48.76 mmol) of ethyl chloroformate were successively added at a temperature of −12° C. After stirring for 2 minutes at this temperature, a cold solution of 21.6 g (48.76 mmol) of HCl.H-Gly-Trp-Met-OMe (IV) and 5.5 ml (48.76 mmol) of NMM in 100 ml of DMF was added. The reaction mixture was stirred for 1 hour at −12° C. and for 2 hours at 0° to 15° C., then filtered from salts and evaporated in vacuo. The crude product was purified by column chromatography on silica gel (Merck) 0.040–0.063 mm eluting with AcOEt. From AcOEt/Et$_2$O/PE 18.13 g (60% yield) of compound V were obtained: m.p. 110° C. $[\alpha]_D^{20} = -31.6°$ (c=1, MeOH); Rf$_A$0.14; Rf$_B$ 0.54.

Step 6. HCl.H-Leu-Gly-Trp-Met-OMe (VI)

18 g (29.04 mmol) of BOC-Leu-Gly-Trp-Met-OMe (V) were dissolved in 290 ml of a saturated solution of hydrogen chloride in glacial acetic acid to which 18 ml of anisole and 9 ml of 2-mercaptoethanol were added. After 30 minutes at room temperature the BOC-removal was complete and the solvent was removed in vacuo at 30° C. The crude product was purified by column chromatography on silica gel (Merck) 0.040–0.63 mm eluting with chloroform; methanol=8:2. From iPrOH-/iPr$_2$O, 12.44 g (77% yield) of compound VI were obtained: m.p. 170° C.; $[\alpha]_D^{20} = -9.9°$ (c=1, MeOH); Rf$_D$ 0.62; E$_{1.2}$ 0.71.

Step 7. BOC-Pro-Pro-OBzl (VII)

To a solution of 21.52 g (100 mmol) of BOC-ProOH in 200 ml of anhydrous THF, 11.2 ml of NMM and 13.3 ml of iso-butyl chloroformate were successively added at a temperature of −10° C. After stirring for 3 minutes at this temperature, a cold solution of 24.17 g (100 mmol) of HCl.H-Pro-OBzl (J. Ramachandran and C.H. Li, J. Org. Chem. (1963), 28, 173) and 11.2 ml (100 mmol) of NMM in 150 ml of DMF were added. The reaction mixture was stirred for 1 hour at −10° C. and for 2 hours at 0° to 15° C., then filtered from salts and evaporated in vacuo. The residue was dissolved in ethyl acetate and washed several times successively with sodium chloride saturated solutions of 1M citric acid, 1M sodium bicarbonate and water. The organic layer was dried over anhydrous sodium sulphate and the solvent removed in vacuo, 34.21 g (85% yield) of compound VII were obtained as an oil. Rf$_A$ 0.62.

Step 8. HCl.H-Pro-Pro-OBzl (VIII)

34.21 g (85 mmol) of BOC-Pro-Pro-OBzl (VII) were dissolved in 342 ml of a saturated solution of hydrogen chloride in acetic acid at room temperature. After 30 minutes BOC-removal was complete and the solvent was removed in vacuo. From iPrOH/AcOEt 21.60 g (75% yield) of compund VIII were obtained: Rf$_D$ 0.32; E$_{1.2}$1.12.

Step 9. BOC-Val-Pro-Pro-OBzl (IX)

Starting from 13.79 g (63.45 mmol) of BOC-Val-OH and 21.5 g (63.45 mmol) of HCl.H-Pro-Pro-OBzl (VIII) and operating as described in Step 7, 22.28 g (70% yield) of compound IX were obtained as an oil after purification by column chromatography on silica gel (Merck) 0.040–0.063 mm eluting with ethyl acetate: methanol=98:2.

Step 10. BOC-Val-Pro-Pro-OH (X)

22.28 g (44.42 mmol) of BOC-Val-Pro-Pro-OBzl (IX) dissolved in 150 ml of methanol were hydrogenated at room temperature and atmospheric pressure in the presence of 4.46 g of 10% by weight palladium-on-charcoal. The catalyst was removed by filtration and the solution was concentrated in vacuo. The residue was dissolved in ethyl acetate and concentrated in vacuo. By dilution with diethyl ether, 10.98 g (60% yield) of compound X were obtained: m.p. 184°–190° C. $[\alpha]_D^{20} = -149.9°$ (c=1, MeOH); Rf$_B$ 0.24; Rf$_C$ 0.53; E$_{5.8}$ 0.51.

Step 11. BOC-Val-Pro-Pro-Leu-Gly-Trp-Met-OMe (XI)

Starting from 9.10 g (22.12 mmol) of BOC-Val-Pro-Pro-OH (X) and 12.30 g (22.12 mmol of HCl.H-Leu-Gly-Trp-Met-OMe (VI) and operating as described in Step 5, but using as an eluant system ethyl acetate containing an increasing amount of methanol from 5 to 30 percent during the chromatographic purification, 16.16 g (80% yield) of compound XI were obtained from iPrOH/iPr$_2$O: m.p. 184°–190° C. $[\alpha]_D^{20} = -98.9°$ (c=1, MeOH); Rf$_B$ 0.13; Rf$_C$ 0.58.

Step 12. BOC-Val-Pro-Pro-Leu-Gly-Trp-Met-OH (XII)

5.00 g (5.48 mmol) of BOC-Val-Pro-Pro-Leu-Gly-Trp-Met-OMe (XI) were dissolved in 20 ml of methanol and saponified with 10 ml of 1M sodium hydroxide for 2 hours at room temperature. The solution was diluted with water, partially concentrated in vacuo, cooled to 0° C., acidified to pH 2 with 5M aqueous hydrochloric acid, and then extracted several times with ethyl acetate. The organic layer was washed to neutrality with saturated aqueous solution of sodium chloride and dried over anhydrous sodium sulphate. Removal of the solvent gave 3.99 g (81% yield) of compound XII: m.p. 194°–200° C. (d); $[\alpha]_D^{20} = -102.9°$ (c=1, MeOH); Rf$_C$ 0.34; E$_{5.8}$ 0.18 Glu.

Step 13. H-Val-Pro-Pro-Leu-Gly-Trp-Met-OH.HCl (XIII)

Starting from 3.85 g (4.28 mmol) of BOC-Val-Pro-Pro-Leu-Gly-Trp-Met-OH (XII) and operating as described in Step 6, 3.05 g of crude compound XIII obtained from iPrOH/iPr$_2$O. The crude product was then purified on DEAE-Sephadex A-25 (Trade Mark) using as an eluant a 0.02M solution of ammonium acetate at pH 6.7. After lyophilization from acetic acid, the product was redissolved in acetic acid and treated with 6 ml of a saturated solution of hydrochloric acid in acetic acid. The solution was poured into diethyl ether.

2.57 g (72% yield) of compound XIII were obtained: m.p. 150° C.; $[\alpha]_D^{22} = -90.5°$ (c=1, MeOH); Rf$_D$ 0.30; E$_{1.2}$ 0.58 Glu.

EXAMPLE 2

Preparation of HCl.H-Val-Pro-Pro-Leu-Gly-Trp-Met-OMe, TK7-Der (XIV)

Starting from 5.00 g (4.28 mmol) of BOC-Val-Pro-Pro-Leu-Gly-Trp-Met-OMe (XI) prepared in Example 1, Step 11, and operating as described in Example 1, Step 6, but using as an eluant system CH$_2$Cl$_2$:MeOH:H$_2$O=86:14:1 during the chromatographic purification, 2.73 g (75% yield) of compound XIV were obtained from AcOEt: m.p. 154° C.; $[\alpha]_D^{22} = -92.4°$ (c=1, MeOH); Rf$_D$ 0.34; E$_{1.2}$ 0.58 Glu.

EXAMPLE 3

Preparation of HCl.H-Val-Pro-Pro-Leu-Gly-Trp-Met-NH$_2$ (XVI)

Step 1. BOC-Val-Pro-Pro-Leu-Gly-Trp-Met-NH$_2$ (XV)

5.00 g (4.28 mmol) of BOC-Val-Pro-Pro-Leu-Gly-Trp-Met-OMe (XI) prepared in Example 1, Step 11, were dissolved in a solution of 100 ml of methanol and 2 ml of ethylene glycol, and saturated at 0° C. with ammonia. The reaction mixture was kept in the refrigerator for 3 days, and then the excess of ammonia and the solvent were removed in vacuo. The crude product was partially purified by column chromatography on silica gel (Merck) 0.040–0.063 mm eluting with AcOEt:MeOH=87:13 and used as such in the next Step (2.58 g of compound XV were obtained from iPrOH/iPr$_2$O): Rf$_C$ 0.31.

Step 2. H-Val-Pro-Pro-Leu-Gly-Trp-Met-NH$_2$.HCl (XVI)

Starting from 2.45 g (2.73 mmol) of BOC-Val-Pro-Pro-Leu-Gly-Trp-Met-NH$_2$ (XV) and operating as described in Example 1, Step 6, but using as eluant systems CH$_2$Cl$_2$:MeOH:H$_2$O=85:15:1 by volume and CH$_2$Cl$_2$:MeOH:H$_2$O=80:20:1 by volume during the chromatographic purification, 1.55 g (68% yield) of compound XVI were obtained from MeOH/iPrOH/iPr$_2$O after desalting on Sephadex G-10 (Trade Mark): m.p. 150°–158° C.; $[\alpha]_D^{24} = -74.8°$ (c=1, MeOH); RF$_D$ 0.36; E$_{1.2}$ 0.55 Glu.

EXAMPLE 4

Growth test in pigs

The growth test was carried out for a period of 3 weeks, using groups of 7 castrated male pigs (Hybrids) divided in subgroups and managed in cages with flat decks. The pigs were fed during the whole experimental period with grower feed (Höveler, normal type without feed additives), 1 kg per day. Water was given ad libitum. The weights were weekly recorded. Experimental protocol is reported in the following table.

| Group | No. of animals | Treatment with | Dosage | Parameters |
|---|---|---|---|---|
| 1 | 2 | — | — | body weight |
| 2 | 2 | NaCl phys. | 0.1 ml/kg (b.w.) | feed consumption |
| 3 | 3 | TK-7 (Ex. 1) | 50 ng/kg (b.w.) | feed efficiency (kg feed/kg weight gain) |

| Results Group | 1 | 2 | 3 |
|---|---|---|---|
| Treatment | — | NaCl phys. | TK-7 (Ex. 1) |
| Dosage (ng/kg) | — | — | 50 |
| Initial weight (kg) | 12.5 | 14.8 | 11.7 |
| Weight after 1 week | 14.0 | 16.3 | 15.2 |
| Weight after 2 weeks | 16.0 | 18.5 | 17.8 |
| Weight after 3 weeks | 19.3 | 20.5 | 20.7 |
| Weight gain in kg | 6.8 | 5.7 | 9.0 |
| Weight gain in % | 54.4 | 38.5 | 76.9 |
| Δ % to control group | | −16.2 | +32.4 |
| Consumption (kg) | 21 | 21 | 21 |
| Feed efficiency | 3.09 | 3.68 | 2.33 |
| Δ % to control group | | +19.1 | −24.6 |

The daily injection of physiological saline solution caused a decrease in weight gain in comparison to the untreated group. In spite of this reduced growth due to the stress from the injection, the animals with daily injection of TK-7 showed a clear increase in weight gain. The feed efficiency reflects the results of the weight gain.

What is claimed as new and desired to be secured by letters patent of the United States is:

1. A peptide of the formula:

ti X-Val-Pro-Pro-Leu-Gly-Trp-A-Y wherein

X is selected from the group consisting of a hydrogen atom or a terminal nitrogen protecting group selected from the group consisting of acyl, aliphatic urethane, aromatic urethane, alkyl, and aralkyl groups;

A is a neutral L-α-amino acid residue selected from the group consisting of Met, Nle, Leu and Phe; and Y is selected from the group consisting of a hydroxy group, an amino group or a group of the formula OR, NHR, NR$_2$ or NH—NH—R' wherein (i) R represents a straight alkyl chain, a branched alkyl chain, a cyclic alkyl group, a fused alkyl ring, or a bridged alkyl ring, each having up to 11 carbon atoms and being unsubstituted or independently substituted by a hydroxy or an amino group or a halogen atom, or R represents an aralkyl group having from 7 to 14 carbon atoms or a phenyl group; and (ii) R' represents a hydrogen atom, a straight alkyl chain, a branched alkyl chain, a cyclic alkyl group, a fused alkyl ring, or a bridged alkyl ring, each having up to 11 carbon atoms and being unsubstituted or independently substituted by a hydroxy or an amino group or a halogen atom, or R' represents an aralkyl group having from 7 to 14 carbon atoms or a phenyl group, or R' represents a straight chain aliphatic acyl group, a branched chain aliphatic acyl group, or a cyclic aliphatic acyl group, each having from 1 to 11 carbon atoms and being unsubstituted or independently substituted by a hydroxy or an amino group or a halogen atom, an aromatic acyl group which is unsubstituted or independently substituted by a hydroxy or amino group or a halogen atom, a straight chain, a branched chain or a cyclic aliphatic urethane type group having from 3 to 11 carbon atoms, or an aromatic urethane group, or a pharmaceutically or veterinarily acceptable salt thereof.

2. A peptide of the formula:

X-Val-Pro-Pro-Leu-Gly-Trp-A-Y wherein X is a hydrogen atom, or a formyl, acetyl, trifluoroacetyl, propionyl, benzoyl, benzyloxycarbonyl, 4-nitrobenzyloxycarbonyl, 4-methoxybenzyloxycarbonyl, 2,4-dichlorobenzyloxycarbonyl, 2-bromobenzyloxycarbonyl, 9-fluorenylmethoxycarbonyl, 3,5-dimethoxy-α, α'-dimethylbenzyloxycarbonyl, t-butoxycarbonyl, 1-methylcyclobutoxycarbonyl, adamantyloxycarbonyl, isobornyloxycarbonyl, methylsulphonylethoxycarbonyl, trityl, benzyl, methyl, or isopropyl group;

A is selected from the group consisting of Met, Nle, Leu, and Phe residues;

Y is selected from the group consisting of a hydroxy group, an amino group or a group of the formula OR, NHR, NR$_2$ or NH—NH—R' wherein R is a methyl, an ethyl, a n-propyl, an isopropyl, a n-butyl, a s-butyl, an isobutyl, a t-butyl, a 2,2,2-trifluoroethyl, a cyclohexyl, an adamantyl, a phenyl, a benzyl, a fluorenylmethyl, or a phenethyl group and R' is a hydrogen atom, a methyl, an ethyl, a n-propyl, an isopropyl, a n-butyl, a s-butyl, an isobutyl, a t-butyl, a 2,2,2-trifluoroethyl, a cyclohexyl, an adamantyl, a phenyl, a benzyl, a fluoromethyl, a phenethyl group, a formyl, an acetyl, a trifluoroacetyl, a propionyl, a butyryl, an adamantylcarbonyl, a benzoyl, a phenylacetyl, a cinnamyl, a benzyloxycarbonyl, a 4-nitrobenzyloxycarbonyl, a 4-methoxybenzyloxycarbonyl, a 2,4-dichlorobenzyloxycarbonyl, a 2-bromobenzyloxycarbonyl, a 9-fluorenylmethoxycarbonyl, a 3,5-dimethoxy-α,α'-dimethylbenzyloxycarbonyl, a t-butoxycarbonyl, a 1-methylcyclobutoxycarbonyl, an adamantyloxycarbonyl, a methylsulphonylethoxycarbonyl, or an isobornyloxycarbonyl group;

or an acid or base addition salt thereof, said acid addition salt being derived from sulphuric, phosphoric, hydrochloric, hydrobromic, hydroiodic, nitric, sulphamic, citric, lactic, pyruvic, oxalic, maleic, succinic, tartaric, cinnamic, acetic, trifluoroacetic, benzoic, salicylic, gluconic or ascorbic acid and said base addition salt being derived from sodium hydroxide, potassium hydroxide, diethylamine, triethylamine or dicyclohexylamine.

3. The compound of claim 2, wherein X is a hydrogen atom.

4. The compound of claim 3 wherein A is a Met residue.

5. A compound of formula:

H-Val-Pro-Pro-Leu-Gly-Trp-Met-OMe, or a pharmaceutically or veterinarily acceptable salt thereof.

6. A compound of formula:

H-Val-Pro-Pro-Leu-Gly-Trp-Met-OH or a pharmaceutically or veterinarily acceptable salt thereof.

7. A peptide selected from the group consisting of:
H-Val-Pro-Pro-Leu-Gly-Trp-Met-NH$_2$,
H-Val-Pro-Pro-Leu-Gly-Trp-Nle-OH,
H-Val-Pro-Pro-Leu-Gly-Trp-Nle-OMe,
H-Val-Pro-Pro-Leu-Gly-Trp-Nle-NH$_2$,
H-Val-Pro-Pro-Leu-Gly-Trp-Leu-OH,
H-Val-Pro-Pro-Leu-Gly-Trp-Leu-OMe,
H-Val-Pro-Pro-Leu-Gly-Trp-Leu-NH$_2$,
H-Val-Pro-Pro-Leu-Gly-Trp-Ile-OH,
H-Val-Pro-Pro-Leu-Gly-Trp-Ile-OMe,
H-Val-Pro-Pro-Leu-Gly-Trp-Ile-NH$_2$,
H-Val-Pro-Pro-Leu-Gly-Trp-Phe-OH,
H-Val-Pro-Pro-Leu-Gly-Trp-Phe-OMe, and
H-Val-Pro-Pro-Leu-Gly-Trp-Phe-NH$_2$, or a pharmaceutically or veterinarily acceptable salt thereof.

8. A method of promoting the growth rate of animals comprising administering daily in their feed rations or by subcutaneous implant an effective amount of the peptide of claim 1 or 2 a veterinarily acceptable salt thereof.

9. An animal feed to which is admixed an effective amount of the peptide of claim 1 or 2 a veterinarily acceptable salt threof.

10. A veterinary composition comprising a peptide according to claim 1 or 2 or a veterinarily acceptable salt thereof in admixture with a veterinarily acceptable diluent or carrier.

11. The peptide of claim 7, wherein the said peptide is H-Val-Pro-Pro-Leu-Gly-Trp-Met-NH$_2$ or a pharmaceutically or veterinarily acceptable salt thereof.

12. The peptide of claim 7, wherein the said peptide is H-Val-Pro-Pro-Leu-Gly-Trp-Nle-OH or a pharmaceutically or veterinarily acceptable salt thereof.

13. The peptide of claim 7, wherein the said peptide is H-Val-Pro-Pro-Leu-Gly-Trp-Nle-ONe or a pharmaceutically or veterinarily acceptable salt thereof.

14. The peptide of claim 7, wherein the said peptide is H-Val-Pro-Pro-Leu-Gly-Trp-Nle-NH$_2$ or a pharmaceutically or veterinarily acceptable salt thereof.

15. The peptide of claim 7, wherein the said peptide is H-Val-Pro-Pro-Leu-Gly-Trp-Leu-OH or a pharmaceutically or veterinarily acceptable salt thereof.

16. The peptide of claim 7, wherein the said peptide is H-Val-Pro-Pro-Leu-Gly-Trp-Leu-OMe or a pharmaceutically or veterinarily acceptable salt thereof.

17. The peptide of claim 7, wherein the said peptide is H-Val-Pro-Pro-Leu-Gly-Trp-Leu-NH$_2$ or a pharmaceutically or veterinarily acceptable salt thereof.

18. The peptide of claim 7, wherein the said peptide is H-Val-Pro-Pro-Leu-Gly-Trp-Ile-OH or a pharmaceutically or veterinarily acceptable salt thereof.

19. The peptide of claim 7, wherein the said peptide is H-Val-Pro-Pro-Leu-Gly-Trp-Ile-OMe or a pharmaceutically or veterinarily acceptable salt thereof.

20. The peptide of claim 7, wherein the said peptide is H-Val-Pro-Pro-Leu-Gly-Trp-Ile-NH$_2$ or a pharmaceutically or veterinarily acceptable salt thereof.

21. The peptide of claim 7, wherein the said peptide is H-Val-Pro-Pro-Leu-Gly-Trp-Phe-OH or a pharmaceutically or veterinarily acceptable salt thereof.

22. The peptide of claim 7, wherein the said peptide is H-Val-Pro-Pro-Leu-Gly-Trp-Phe-OMe or a pharmaceutically or veterinarily acceptable salt thereof.

23. The peptide of claim 7, wherein the said peptide is H-Val-Pro-Pro-Leu-Gly-Trp-Phe-NH$_2$ or a pharmaceutically or veterinarily acceptable salt thereof.

* * * * *